United States Patent [19] [11] 4,083,955
Grabenstetter et al. [45] Apr. 11, 1978

[54] PROCESSES AND COMPOSITIONS FOR REMINERALIZATION OF DENTAL ENAMEL

[75] Inventors: Robert John Grabenstetter, Colerain Township, Hamilton County; John Augustus Gray, III, Springfield Township, Hamilton County, both of Ohio

[73] Assignee: The Procter & Gamble Company, Cincinnati, Ohio

[21] Appl. No.: 677,933

[22] Filed: Apr. 19, 1976

Related U.S. Application Data

[63] Continuation of Ser. No. 561,830, Apr. 2, 1975, abandoned, which is a continuation of Ser. No. 438,973, Feb. 4, 1974, abandoned, which is a continuation-in-part of Ser. No. 297,517, Oct. 13, 1972, abandoned.

[51] Int. Cl.$^2$ ............... A61K 7/16; A61K 7/18; A01N 11/00; A61K 33/16
[52] U.S. Cl. ............................. 424/49; 424/52; 424/57; 424/128; 424/151; 424/154
[58] Field of Search .................... 424/128, 49–58

[56] References Cited

U.S. PATENT DOCUMENTS 3,175,951 3/1965 Tucker et al. ............... 424/52
3,679,360 1/1972 Rubin et al. ............... 424/128

FOREIGN PATENT DOCUMENTS 1,090,340 11/1967 United Kingdom.

OTHER PUBLICATIONS

Souder et al., J. Am. Dental Assoc. 31, No. 23, 12/1/44, pp. 1579–1586.
Public Health Reports, 63, No. 38, 9/17/48, pp. 1215–1221.
Feagin et al., Arch. Oral Biology, 16, pp. 535–548, (1971).

Primary Examiner—Albert T. Meyers
Assistant Examiner—D. W. Robinson
Attorney, Agent, or Firm—George W. Allen; Douglas C. Mohl; Eric S. Spector

[57] ABSTRACT

Two compositions containing respectively a cation and an anion, such as calcium ion and phosphate ion, are sequentially applied to dental enamel resulting in remineralization of subsurface dental enamel.

15 Claims, No Drawings

PROCESSES AND COMPOSITIONS FOR REMINERALIZATION OF DENTAL ENAMEL

This application is a continuation of application Ser. No. 561,830, filed Apr. 2, 1975, now abandoned, which is a continuation of application Ser. No. 438,973, filed Feb. 4, 1974, now abandoned, which is a continuation-in-part of application Ser. No. 297,517, filed Oct. 13, 1972, now abandoned.

BACKGROUND OF THE INVENTION

This invention relates to processes and compositions which are useful to remineralize subsurface dental enamel. More specifically, this invention relates to salt solutions, such as calcium and phosphate salt solutions, which are sequentially applied to dental enamel resulting in remineralization of subsurface dental enamel.

It is well known in the dental art that dental caries begins as a subsurface demineralization ("white spot") of the dental enamel and that remineralization may be of importance in retarding or arresting dental caries. U.S. Patent No. 3,679,360, July 25, 1972, to Rubin et al., discloses a method, the purpose of which is to deposit calcium phosphate from a gel medium onto the surface of a tooth. But this method of remineralizing has several disadvantages. Remineralization occurs only on the surface of the tooth whereas the initial cause of dental caries is subsurface demineralization. The surface on which apatite growth is desired must be prepared (as by roughening), and the tooth and coatings must be covered by a suitable cap for several days while the mineralization of the tooth surface occurs.

The disadvantages of the method disclosed in the Rubin et al. patent are overcome by the present invention which effects subsurface remineralization rather than surface remineralization. Since dental caries begins as a subsurface demineralization of the dental enamel, subsurface remineralization arrests and repairs the carious lesion before any permanent structural damage to the tooth occurs. The present invention does not require preparation of the enamel surface, capping of the tooth, or removal of decay products. Further, the present invention may be conveniently practiced by the public without substantially changing their dental care habits.

SUMMARY OF THE INVENTION

Subsurface remineralization of tooth enamel with a desirable precipitate is accomplished by a process utilizing a first composition comprising a water-soluble compound capable of acting as a source of the cation of said desirable precipitate, and a second composition comprising a water-soluble compound capable of acting as a source of the anion of said desirable precipitate. The process comprises the steps of: (1) applying one of the above compositions to the surface of said tooth for a period of time sufficient to allow the desired ion to diffuse into said demineralized subsurface, and thereafter, (2) applying the other composition to the surface of said tooth whereby the desired ion of said other composition diffuses into said demineralized subsurface and forms said desirable precipitate, thus effecting remineralization of the demineralized subsurface. Further, the remineralizing precipitate formed is less susceptible to demineralization than original enamel if heavy metal cations and fluoride anions are employed in the remineralization process.

Concentrations of the cationic and anionic solutions may be from 0.005 to 10% or the limit of solubility of the salt with from about 0.05 to about 5% preferred. More than one cation may be employed in the cationic solution. Similarly, more than one anion may be employed in the anionic solution. There is a visible effect on "white spots" after as few as eight sequential applications, and it is contemplated that several sequential applications will be employed to achieve the most beneficial results.

DESCRIPTION OF THE INVENTION

The present invention lies in the discovery that subsurface dental enamel may be remineralized by the sequential application of certain soluble salts yielding ions which will react to form a desirable remineralizing precipitate. The sequential application consists of two steps which may be performed in any order, although the following order is slightly preferred. In the first step, a reactant solution of a soluble salt is placed in contact with the tooth surface nearest to the demineralized subsurface. In this first reactant solution are selected cations which diffuse through the tooth surface to its demineralized subsurface.

In the second step, a reactant solution containing selected anions is placed in contact with the tooth surface nearest the demineralized subsurface. The anions diffuse through the tooth surface to the demineralized subsurface where they come in contact with the cations previously deposited and form a precipitate which is bound to the tooth structure. As a result, the tooth's subsurface is remineralized.

Concentrations of the salt solutions are from about 0.005 to about 10% or the limit of solubility of the salt. Excess salt can be present, if desired. Concentrations from about 0.05 to about 5% are preferred. The concentrations of the soluble salts containing the desired anions are essentially the same as those for the water-soluble salts containing the desired cations. Equivalent concentrations are not necessary since in each step an excess of the reactant is required in order to promote diffusion into the tooth's demineralized subsurface.

In order to effect remineralization of the dental enamel, a therapeutic amount of the desired cations and anions must be employed in the oral cavity. The amount of solution placed in the mouth must contain at least 0.001 g. of desired cations and 0.001 g. of desired anions and preferably contains more than 0.1 g. of desired cations and 0.1 g. of desired anions.

While the length of time of contact between the salt solutions and the tooth's surface is not critical, it is necessary for the length of time to be great enough to allow diffusion of the ions through the tooth's surface to the demineralized subsurface. It is believed that at least ten seconds is required for this diffusion.

Each solution should have a pH of from about 3 to about 10 before and after the precipitation reaction, and be otherwise compatible in the oral environment. The ions must not combine prematurely in the solution to form a precipitate, but must be able to diffuse through the surface of the tooth to a demineralized subsurface area and be able to form an insoluble salt with ions of the other solution. The solutions and the insoluble precipitates are preferably not colored, and, or course, have acceptable levels of toxicity (i.e., the particular ions, in the amounts used in the remineralization process, must be non-toxic).

Although many precipitates are within the broad scope of this invention, by depositing a precipitate less soluble than the original enamel, the remineralized subsurface can be made to be more resistant to demineralization than was the original enamel. If the remineralization contemplated by this invention is carried out in the presence of either a heavy metal ion or fluoride ion, the remineralized enamel is more resistant to demineralization than was the original enamel. If both ions are present, the remineralized enamel is even more resistant to demineralization. The concentration of salt containing heavy metal ion and fluoride ion in their respective solutions may be from about 0.005 to about 10%, but from about 0.005 to about 0.1% is preferred.

Examples of suitable heavy metal ions are aluminum, manganese, tin, zinc, indium, and rare earth metals such as lanthanum and cerium. Indium is preferred.

In the most preferred embodiment of the present invention, the remineralizing cationic solution contains from about 0.005 to about 10%, preferably about 1%, of a soluble calcium salt yielding calcium ions and from about 0.005 to about 10%, preferably from about 0.005 to 0.1% of a soluble indium salt yielding indium ions. The remineralizing anionic solution contains from about 0.005 to about 10%, preferably about 1%, of soluble phosphate salt yielding phosphate ions and from about 0.005 to about 10%, preferably from about 0.005 to about 0.1% of a soluble fluoride salt yielding fluoride ions.

The resulting precipitate is a calcium phosphate or hydroxylapatite, the natural constituent of tooth enamel, with incorporated indium and fluoride ions. Not only does this process result in remineralized enamel, but the remineralized enamel is more resistant to subsequent demineralization than was the original enamel.

Soluble fluoride and indium salts which are suitable for use in solutions of the present invention include, but are not limited to, sodium fluoride, zinc fluoride, betaine fluoride, alanine stannous fluoride, hexylamine fluoride, indium chloride, indium sulfate, and indium nitrate. Suitable salts for other desired cations and anions would be obvious to one skilled in the art.

The anions which give desirable insoluble precipitates include phosphate, fatty acid groups having from 8 to 18 carbon atoms, fluoride, fluorophosphate, silica fluoride, sulfate, tartrate, sorbate, alkyl sulfonates having from 6 to 18 carbon atoms, carbonates, etc. Mixtures of these anions are desirable.

Cations which give desirable insoluble precipitates include the heavy metal ions referred to hereinbefore, and calcium and magnesium. Mixtures of these cations are desirable.

These cations and anions which form the insoluble remineralizing precipitates are obtained from solutions of the corresponding soluble salts. Suitable soluble salts of the cations used in this invention include the halide, e.g., chloride, nitrate, sulfate, acetate and gluconate salts of the desired cation. Similarly suitable soluble salts of the anions of this invention include alkali metal (e.g., sodium and potassium), ammonium, and low molecular weight substituted ammonium salts. Examples of low molecular weight substituted ammonium salts are those where one or more of the hydrogen atoms on the ammonium ion is substituted with a 1-3 carbon atom, alkyl or hydroxy alkyl group such as methyl, ethyl, propyl, hydroxyethyl, 2-hydroxypropyl, or 3-hydroxypropyl, e.g., the mono-, di-, or triethanolammonium salts or the mono-, di-, or triethylammonium salts.

The many different cations and anions with which one could remineralize tooth enamel combine to form many different precipitates. Most preferred precipitates are calcium phosphate compounds with small amounts of indium and fluoride incorporated therein. The following precipitates disclose not only desirable remineralizing precipitates but, of course, also the cations and anions necessary to form the precipitates. It will be recognized by one skilled in the art that some of these precipitates can be formed by first forming an original precipitate which then further reacts to form the indicated precipitate. For example, a hydroxide may form first and then react further to form the corresponding oxide.

Preferred precipitates are: calcium phosphates; $ZnNH_4PO_4$; $InPO_4$; rare earth phosphates such as lanthanum, cerium and samarium phosphate; rare earth fluorides such as lanthanum, cerium, praseodymium, neodymium, and samarium fluorides; magnesium alkyl sulfonate wherein the alkyl group has from 10 to 22 carbon atoms; magnesium stearate; calcium stearate; zinc stearate; and aluminum phosphates.

As discussed before, the cations of the above precipitates are readily obtained from a solution of the corresponding soluble salts, e.g., the chloride salts. The anions of the above precipitates are readily obtained from solutions of the corresponding soluble salts, e.g., sodium, potassium, ammonium or low molecular weight substituted ammonium salts.

Other precipitates contemplated by this invention are: Aluminum oxide; aluminum hydroxide; indium hydroxide; indium phosphate; lanthanum tartrate; lanthanum sorbate; lanthanum oxide; lanthanum phosphate; magnesium alkyl sulfonates such as magnesium n-decyl sulfonate, magnesium lauryl sulfonate, magnesium myristyl sulfonate, magnesium cetyl sulfonate, and magnesium n-octadecyl sulfonate; magnesium oleate; magnesium myristate; magnesium palmitate; magnesium stearate; magnesium laurate; magnesium carbonate; magnesium fluoride; magnesium phosphates; magnesium ammonium phosphates; manganese carbonate; manganese hydroxide; manganese ammonium phosphate; nickel hydroxide, laurate, myristate, palmitate and stearate; zinc tartrate; zinc carbonate; zinc hydroxide; zinc phosphate (usually complex mixtures); zinc ammonium phosphate; calcium carbonate; calcium silicate; calcium lauryl sulfonate; calcium myristyl sulfonate; calcium n-hexadecyl sulfonate; calcium n-octadecyl sulfonate; calcium oleate; calcium stearate; calcium tartrate; calcium aluminates; calcium hydroxide; calcium ammonium phosphate; tricalcium phosphate; dicalcium phosphate; calcium monofluorophosphate; $MgHPO_4$; $Mg_3(PO_4)_2$; $MgNH_4PO_4$; aluminum phosphates; aluminum orthophosphate; calcium phosphates; zinc phosphates; strontium phosphate; indium phosphate; tin phosphate; ceric phosphate; $SiO_2$; $SiO_2 \cdot XH_2O$; $Sn(OH)_2$ and $SnO \cdot XH_2O$. These precipitates are formed by using the appropriate cations in the first solution and the appropriate anions in the second solution as described above.

Since the cationic and anionic components of the remineralization precipitate must be delivered to the tooth surface in a sequential manner, it is necessary to employ a delivery system which meets this requirement. The components of the precipitate can be sequentially delivered to the surface of the tooth by means of two separate delivery vehicles, each containing one component. Or the delivery system can consist of one vehicle which contains both components but releases them in a sequential manner.

Examples of two vehicle systems, in which cationic components are in one vehicle and anionic components are in another vehicle are: Mouthwash-mouthwash; toothpaste-toothpaste; toothpaste-mouthwash; mouthwash-toothpaste; beverage-beverage; candy drop-candy drop; nutritional substance-nutritional substance; toothpowder-toothpowder; and so forth.

Examples of one vehicle systems where some means is provided for sequential release of the components include, but are not limited to, a metastable system in which ions are released at different times; a toothpaste in which one ingredient is encapsulated for delayed release; a two-compartment bottle; a lozenge with a laminated structure so that first one ionic ingredient is released and then another; a chewing gum made so that one ingredient is released before the other; a nutritional substance in which one ingredient is released before the other; and so forth.

The present invention may also be practiced by direct delivery to the tooth surface. The ionic ingredients can be topically applied in solution, in a gel, by means of tape or other adhesive material, or by means of a water pic or irrigation device.

The remineralization solutions may also contain other useful ingredients such as compatible therapeutic agents, sudsing agents, sweeteners, coloring agents, abrasives, thickeners, preservatives, and stabilizers. Examples of such ingredients are disclosed in U.S. Pat. No. 3,175,951, Tucker et al., Mar. 30, 1965.

For commercial exploitation of the present invention, it is contemplated that "kits" will be made which will enable the consumer to conveniently store and then sequentially apply the respective cationic and anionic solutions to the teeth. Suitable kits can comprise two separately packaged solutions of the respective cations and anions, but more preferably, the kits are in the form of a two-part toothpaste or mouthwash composition. The two parts should be packaged to facilitate sequentially applying the solutions to the teeth.

Several oral compositions which are embodiments of this invention are set forth in the following examples which are given to further illustrate the present invention.

EXAMPLE I

Cationic Mouthwash

| Ingredient | % by Weight |
|---|---|
| Indium trichloride (2.89% solution in $H_2O$) | 1.000 |
| Calcium chloride | 1.109 |
| Glycerin, U.S.P. | 10.000 |
| Ethanol, 190-proof, U.S.P. | 7.500 |
| Flavor | 0.170 |
| Polyoxyethylene (20) Sorbitan monoisostearate | 0.450 |
| Sodium saccharin, N.P. | 0.090 |
| Boric acid, U.S.P. | 0.075 |
| Glacial acetic acid, A.C.S. | 0.200 |
| NaOH (10% solution in $H_2O$) | 0.400 |
| FD&C Yellow 15 (1% solution) | 0.140 |
| Distilled water | 78.866 |
| | 100.000 |

Anionic Mouth Rinse

| Ingredient | % by Weight |
|---|---|
| Sodium fluoride | 0.033 |
| Disodium phosphate | 0.847 |
| Glycerin, U.S.P. | 10.000 |
| Ethanol, 190-proof, U.S.P. | 7.500 |
| Flavor | 0.040 |
| Polyoxyethylene (20) sorbitan monoisostearate | 0.200 |
| Sodium saccharin, N.P. | 0.050 |
| Boric acid, U.S.P. | 0.075 |
| FD&C Green (1% solution) | 0.045 |
| Distilled water | 81.210 |
| | 100.000 |

EXAMPLE II

Anionic Dentifrice

| Ingredient | % by Weight |
|---|---|
| Disodium phosphate | 3.120 |
| Sodium fluoride | 0.200 |
| Abrasive (precipitated silica gel) | 19.000 |
| Sorbitol (30% in water) | 25.000 |
| Glycerin | 11.000 |
| Hydroxyethylcellulose | 1.500 |
| Keltrol (a polysaccharide) | 0.650 |
| Sodium alkyl sulfate (28% in water) | 3.500 |
| Saccharin | 0.250 |
| Titanium dioxide | 0.500 |
| Flavor | 0.900 |
| Color | 0.350 |
| Concentrated hydrochloric acid | 2.336 |
| Water | balance |

Cationic Dentifrice

| Ingredient | % by Weight |
|---|---|
| Calcium chloride | 5.000 |
| Indium trichloride (2.89% solution in $H_2O$) | 6.000 |
| Abrasive (precipitated melamine formaldehyde condensation product) | 37.000 |
| Sorbitol (30% in water) | 24.500 |
| Glycerin | 5.700 |
| Hydroxyethylcellulose | 1.300 |
| Kelfrol (a polysaccharide) | 0.600 |
| Sodium alkyl sulfate (28% in $H_2O$) | 4.200 |
| Saccharin | 0.220 |
| Flavor | 0.970 |
| Color | 0.500 |
| Water | balance |

Hydrochloric acid to pH 3.5

EXAMPLE III

Multilayered Lozenge
Cationic Portion

| Ingredient | % by Weight |
|---|---|
| Sorbitol | 17.5 |
| Mannitol | 17.5 |
| Starch | 13.6 |
| $CaCl_2 \cdot 2H_2O$ | 4.7 |
| $InCl_3$ | 0.04 |
| Sugar substitute (Nichaus) | 1.2 |
| Flavor | 11.7 |
| Color | 0.1 |
| Corn syrup | balance |

Anionic Portion

| Ingredient | % by Weight |
|---|---|
| Sorbitol | 17.6 |
| Mannitol | 17.6 |
| Starch | 13.7 |
| $Na_2HPO_4$ | 3.9 |
| NaF | 0.4 |
| Sugar substitute (Nichaus) | 1.2 |
| Flavor | 12.7 |
| Color | 0.1 |
| Corn syrup | balance |

EXAMPLE IV

Toothpowder

Cationic Portion

| Ingredient | % by Weight |
|---|---|
| Sodium alkyl sulfate | 1.00 |
| Indium trichloride | 0.0289 |
| Sodium citrate | 1.50 |
| Flavor | 1.50 |
| Saccharin | 0.29 |
| Abrasive | balance |

Anionic Portion

| Ingredient | % by Weight |
|---|---|
| Sodium alkyl sulfate | 1.00 |
| Disodium phosphate | 3.82 |
| Sodium fluoride | 0.20 |
| Sodium citrate | 1.50 |
| Flavor | 1.50 |
| Saccharin | 0.29 |
| Abrasive | balance |

EXAMPLE V

Chewing Gum

Cationic Portion

| Ingredient | % by Weight |
|---|---|
| Gum base<br>  30 parts Estergum<br>  45 parts Coumarone resin<br>  15 parts dry Latex<br>  10 parts Paraffin wax (M.P. = 180° F) | 30.00 |
| Sugar | 50.00 |
| Corn syrup | 18.00 |
| $InCl_3$ | 0.0289 |
| $CaCl_2$ | 5.00 |
| Citric acid | 1.00 |
| Flavor | balance |

Anionic Portion

| Ingredient | % by Weight |
|---|---|
| Gum base 30.00<br>  30 parts Estergum<br>  45 parts Coumarone resin<br>  15 parts dry Latex<br>  10 parts Paraffin wax (M.P. = 180° F) | |
| Sugar | 50.00 |
| Corn syrup | 18.00 |
| $Na_2HPO_4$ | 3.82 |
| NaF | 0.20 |
| Citric acid | 1.00 |
| Flavor | balance |

Combinations of any of the above anionic with any of the above cationic compositions can also be used. When the above compositions are used in sequence in the human mouth in their normal amounts, demineralized subsurfaces of teeth are remineralized and the resulting tooth structures are less susceptible to re-demineralizations. The concentration of the combination of the calcium and indium salts and the combination of the phosphate and fluoride salts in the human mouth in use are respectively about 2% and about 1%.

EXAMPLE VI

A cationic mouthwash and anionic mouth rinse are made as in Example I except that the ingredients indium trichloride and sodium fluoride are omitted, distilled water being substituted therefor. When the mouthwash and mouth rinse are applied sequentially to the surface of the teeth in accordance with the present invention, demineralized subsurfaces of the teeth are remineralized with calcium phosphate.

EXAMPLE VII

A subject rinses his mouth with 20 cc. of the cationic mouthwash of Example I and then rinses his mouth with 20 cc. of the anionic mouth rinse of Example I. Each rinse is performed for about 30 seconds. The cationic-anionic sequence is performed twice a day for 4 days.

EXAMPLE VIII

A tooth remineralizing "kit" is made by packaging the cationic mouthwash and anionic mouth rinse of Example I in a bottle which has been divided into two separate compartments constructed so that the contents of each compartment can be dispensed independently of the other. 8 oz. of the cationic mouthwash is placed in one compartment and 8 oz. of the anionic mouth rinse is placed in the other compartment.

What is claimed is:

1. Process for remineralizing demineralized subsurface of the tooth with a precipitate bound to the tooth structure, said process comprising the steps of applying first ions to the tooth surface so that said first ions diffuse through the tooth surface to demineralized subsurface and thereafter applying second ions to the tooth surface so that said second ions diffuse through the tooth surface to demineralized subsurface and form a precipitate with previously applied first ions at said subsurface, said first ions comprising one of either calcium ions or phosphate ions, said second ions comprising the other of either calcium ions or phosphate ions, said calcium ions being applied in the form of a solution comprising from about 0.005 to about 10% of a water-soluble calcium salt which is compatible in the oral environment, said phosphate ions being applied in the form of a solution comprising from about 0.005 to about 10% of a water-soluble phosphate salt which is compatible in the oral environment, each of the applications being carried out for a time period consistent with normal dental care habits on the order of about 10 to about 30 seconds.

2. Process as recited in claim 1, in which said first ions comprise calcium ions.

3. Process as recited in claim 1, in which said first ions comprise calcium ions and indium ions.

4. Process as recited in claim 3, in which said first ions are applied in the form of a solution comprising from about 0.005 to about 10% of a water-soluble calcium salt and from about 0.005 to about 10% of a water-soluble indium salt, said salts being compatible in the oral environment.

5. Process as recited in claim 1, in which said second ions comprise phosphate ions and fluoride ions.

6. Process as recited in claim 5, in which said second ions are applied in the form of a solution comprising from about 0.005 to about 10% of a water-soluble phosphate salt and from about 0.005 to about 0.1% of a water-soluble fluoride salt, said salts being compatible in the oral environment.

7. Process as recited in claim 1, in which the first ions comprise calcium ions and indium ions and the second ions comprise phosphate ions and fluoride ions.

8. Process as recited in claim 1, in which said calcium salt is calcium chloride and in which said phosphate salt is disodium phosphate.

9. Process as recited in claim 1, comprising applying the first ions in the form of a toothpaste and applying the second ions in the form of a mouthwash.

10. Process as recited in claim 1, comprising applying the first ions in the form of a toothpaste and applying the second ions in the form of a toothpaste.

11. Process as recited in claim 1, comprising applying the first ions in the form of a mouthwash and applying the second ions in the form of a mouthwash.

12. Process as recited in claim 1, comprising applying the first ions in the form of a mouthwash and applying the second ions in the form of a toothpaste.

13. Process as recited in claim 1, in which the first ions are applied by placing in the mouth a solution containing at least 0.001 gram first ions and in which the second ions are applied by placing in the mouth a solution containing at least 0.001 gram second ions.

14. Process as recited in claim 1, in which the first ions are applied by placing in the mouth a solution containing at least 0.1 gram first ions and in which the second ions are applied by placing in the mouth a solution containing at least 0.1 gram second ions.

15. Process as recited in claim 1, in which fluoride ions are applied along with the phosphate ions.

* * * * *

Notice of Adverse Decision in Interference

In Interference No. 100,348, involving Patent No. 4,083,955, R. J. Grabenstetter and J. A. Gray, PROCESSES AND COMPOSITIONS FOR REMINERALIZATION OF DENTAL ENAMEL, final judgment adverse to the patentees was rendered Aug. 6, 1982, as to claims 1, 2, 5, 6, 8-12 & 15.

[*Official Gazette Feb. 1, 1983.*]